United States Patent
Bombardelli et al.

(10) Patent No.: US 8,337,903 B2
(45) Date of Patent: Dec. 25, 2012

(54) ANTITUMORAL AGENTS WITH A BENZOPHENANTHRIDINE STRUCTURE AND FORMULATIONS CONTAINING THEM

(75) Inventors: Ezio Bombardelli, Groppello Cairoli (IT); Gabriele Fontana, Milan (IT); Paolo Morazzoni, Milan (IT); Antonella Riva, Milan (IT)

(73) Assignee: Indena S.p.A., Milan (IT)

( * ) Notice: Subject to any disclaimer, the term of this patent is extended or adjusted under 35 U.S.C. 154(b) by 223 days.

(21) Appl. No.: 12/918,453

(22) PCT Filed: Feb. 16, 2009

(86) PCT No.: PCT/EP2009/001079
§ 371 (c)(1),
(2), (4) Date: Aug. 19, 2010

(87) PCT Pub. No.: WO2009/103476
PCT Pub. Date: Aug. 27, 2009

(65) Prior Publication Data
US 2010/0331525 A1    Dec. 30, 2010

(30) Foreign Application Priority Data
Feb. 22, 2008   (IT) .............................. MI2008A0284

(51) Int. Cl.
*A61K 35/12* (2006.01)

(52) U.S. Cl. ....................................................... 424/573
(58) Field of Classification Search .................. None
See application file for complete search history.

(56) References Cited

FOREIGN PATENT DOCUMENTS
WO    WO-98/42339 A1    10/1998

OTHER PUBLICATIONS

Kemeny-Beke A et al: "Apoptotic response of uveal melanoma cells upon treatment with chelidonine, sanguinarine and chelerythrine" Cancer Letters, New Tork, NY, US, vol. 237, No. 1, Jun. 8, 2006, pp. 67-75.
N. Ahmad et al: "Differential Antiproliferative and Apoptotic response of Sanguinarine for Cancer Cells versus Normal Cells" Clinical Cancer Research, vol. 6, Apr. 2000, pp. 1524-1528.
Slaninova Iva et al: "Screening of minor benzo(c)phenanthridine alkaloids for antiproliferative and apoptotic activities" Pharmaceutical Biology, Swets and Zeitlinger, Lisse, NL, vol. 45, No. 2, Jan. 1, 2007, pp. 131-139.
Zhihu Ding et al: "The alkaloid sanguinarine is effective against multidrug resistance in human cervical cells via bimodal death" Biological Pharmacology, vol. 63, 2002, pp. 1415-1421.

*Primary Examiner* — Brian-Yong S Kwon
*Assistant Examiner* — Jennifer Berrios
(74) *Attorney, Agent, or Firm* — Arent Fox LLP

(57) ABSTRACT

The use of benzophenanthridine alkaloids and the salts thereof for the preparation of medicaments for the treatment of tumors is disclosed.

8 Claims, No Drawings

ANTITUMORAL AGENTS WITH A BENZOPHENANTHRIDINE STRUCTURE AND FORMULATIONS CONTAINING THEM

CROSS-REFERENCE TO RELATED APPLICATION

This application is a National Stage entry of International Application No. PCT/EP2009/001079, filed Feb. 16, 2009, which claims priority to Italian Application No. MI2008A 000284, filed Feb. 22, 2008, the disclosure of the prior application is hereby incorporated in its entirety by reference.

The present invention relates to the use of benzophenanthridine alkaloids and the salts thereof for the preparation of medicaments for the treatment of tumors.

The invention also relates to the novel salts of said alkaloids and compositions containing them.

STATE OF THE ART

The first aim of oncology is complete eradication of the tumor by any means, even when this entails serious side effects; the motto primum non nocere ("first, do no harm") is not used as a guideline in the treatment of tumors, but preferably replaced with primum succerere ("first, hasten to help").

Oncological treatment usually involves radical surgery, targeted radiotherapy including photodynamic therapy, high doses of chemotherapy drugs, radiotherapy, and treatment with cytokines (IL2) and monoclonal antibodies. Despite the large, constantly increasing number of available treatments, the success rate in terms of cures is still unsatisfactory, especially in the case of the chemotherapy, due to the onset of drug resistance.

In solid tumors, chemotherapy reduces the tumor mass rapidly, but not completely; a few particularly resistant cells can keep the tumor active and it then develops, often with fatal results. These cells were recently classified as tumor stem cells, which possess strong proliferation potential and adaptability. Said cells constitute approx. 5% of the tumor mass, and are resistant to all known chemotherapy agents in current use. The existence of tumor stem cells was established for the first time in myeloid leukaemia (Bonnet D, Dick J. E. *Nature Medicine*, 3, 730-737 (1997)), and subsequently demonstrated in breast and brain tumors (Al-Hajj M, et al., *Natl Acad Sci*, USA, 100. 3983-3988, 2003, Sing S. K., et al., 432, 396-401, Nature 2004).

More recently, stem cells have been isolated from melanomas, colon tumors and pulmonary microtomes (Ricci-Vitali, Nature 445, 111-115 (2007); Fang D., Cancer Res., 65, 9328-9337 2005, Eramo, *Cell Death and Differentiation, advance online publication* Nov. 30. 2007 *Doi:* 10.1038/sj.cdd.4402283).

These cells, as stated above, are not controlled by the standard treatment, and regenerate the tumor. There is consequently a clear need to develop compounds able to inhibit tumor stem cells, possibly by inducing apoptotic processes.

DESCRIPTION OF THE INVENTION

It has now been found that benzophenanthridine alkaloids, especially sanguinarine, chelerythrine, chelidonine and the salts thereof with luteic, phosphatidic or hyaluronic acids have an antiproliferative effect on multiresistant tumor stem cells.

In particular, the salts with luteic acid give the molecules a potent cytotoxic action towards cancer cells and an equally potent antiangiogenic, anti-inflammatory and analgesic action.

In a first aspect, the invention therefore relates to the use of benzophenanthridine alkaloids or the salts thereof for the preparation of medicaments for the treatment of tumors.

In a second aspect, the invention provides novel salts of benzophenanthridine alkaloids with phosphatidic or hyaluronic acids. Said salts are particularly useful for targeted topical or systemic administration.

In a further aspect, the invention provides complexes of benzophenanthridine or isoquinoline alkaloids with human albumin in nanoparticulate form and suspensions containing said complexes which can be administered intravenously or orally. The nanoparticles selectively reach the tumor, where they perform a cytotoxic and anti-angiogenic tumor mass reducing action. This formulation is particularly useful for the treatment of solid tumors and the more common forms of leukaemia.

Phosphatidic acids contain residues of fatty acids, which can be the same or different, with saturated or unsaturated straight chains comprising 12 to 22 carbon atoms.

Dipalmitoyl- and distearoyl-phosphatidic acids which considerably increase oral and topical bioavailability are preferred.

The salt of sanguinarine with a phosphatidic acid is particularly preferred.

The salts according to the invention are able to induce apoptosis of tumor stem cells at sub-micromolar concentrations.

The salt of sanguinarine with luteic acid has proved in vitro a potent inhibiting activity towards melanoma and colon stem cells at a concentration of 200 ng/ml. Its behaviour towards other oncological stem cells is identical. These alkaloids can consequently be considered new-generation antitumoral agents, which are able to treat human tumors effectively. For tumors of the colon, liver, pancreas and cervix the most appropriate form is the salt with luteic acid dispersed in a suitable vehicle, whereas for the treatment of skin tumors such as melanoma, the salt with a phosphatidic acid can advantageously be administered topically directly to the area affected by the tumor.

Complexes with albumin are suitable to be administered by loco-regional injection at a dose much lower than the toxic dose, and for very long periods; selectivity towards tumor stem cells compared with normal cells and the potent anti-angiogenic effect produce a rapid reduction and eventual eradication of the tumor mass.

The product most suitable for oral and topical administration is the salt of sanguinarine with luteic acid. Said salt has proved particularly effective in the treatment of oropharynx, head and neck tumors, melanoma and cervical tumors, to a greater extent than the unsalified alkaloid, and it also interacts with any viruses associated with the tumor.

Salts with hyaluronic acid which increase cell uptake of the alkaloid and allow eradication of the tumor are also advantageous.

The formulations will be prepared by well-known processes such as those described in "Remington's Pharmaceutical Handbook", Mack Publishing Co., N.Y., USA, together with suitable excipients.

The examples set out below illustrate the invention in detail.

EXAMPLE I

Preparation of luteic acid sanguinarine salt 3.68 g of sanguinarine chloride are dissolved in 100 ml of ethanol and added under stirring with 3.6 g of potassium luteate and the mixture is reacted for 3 hours. The formed potassium chloride is filtered off and the solution is concentrated to small volume. 5.6 g of salt are obtained.

EXAMPLE II

Preparation of 1, 2-dipalmitoyl-sn-glycero-3-phospho-rac-(1-glycerol) sanguinarine salt 3.7 g of sanguinarine chloride are dissolved in 50 ml of methanol; this solution is added under stirring with 7.5 g of 1,2-dipalmitoyl-sn-glycero-3-phospho-rac-(1-glycerol) 1,2-dipalmitoyl-sn-glycero-3-phospho-rac-(1-glycerol) sodium salt and the mixture is left under stirring for 2 h. The resulting solution is diluted with an equal volume of methylene chloride and the mixture is left under stirring for 0.5 h. The precipitated sodium chloride is filtered off and the filtrate is concentrated to dryness under vacuum at a temperature not higher than 35° C. 10 g of a reddish solid having melting point of 70° C. are obtained.

EXAMPLE III

Preparation of nanoparticles of albumin with sanguinarine 1 g of sanguinarine are dissolved in 15 ml of dioxane at room temperature and added to a solution of 5 g of human albumin in 300 ml of saline. The mixture is left under stirring in sterile environment for 4 hours. The resulting turbid solution is subjected to ultrasounds for 1 minute. The physical appearance and the color of the suspension change. The solution is freeze-dried without adding excipients.

EXAMPLE IV

Following the procedures of Example III, the sanguinarine solution is prepared and the solute is freeze-dried under sterile conditions in containers which will contain 10 mg of sanguinarine after completion of the process.

The lyophilisate is used in the loco-regional treatment of the oropharynx tumor.

EXAMPLE V

1 Gram Chewable Tablets for the Treatment of Head and Neck Tumor

| | |
|---|---|
| Sanguinarine luteate | 10.00 mg |
| Soy lecithin | 30.00 mg |
| Anhydrous citric acid | 10.00 mg |
| Lactose | 240.00 mg |
| Mannitol | 550.00 mg |
| Methyl cellulose | 40.00 mg |
| Palmitoyl stearate | 50.00 mg |
| Berry flavour | 40.00 mg |
| Ammonium Glycyrrhizinate | 0.5 mg |
| Talc | 10.00 mg |

EXAMPLE VI

Soft-gelatin Capsules for the Treatment of Cervical Tumor

| | |
|---|---|
| Sanguinarine luteate | 10.00 mg |
| Soy lecithin | 50.00 mg |
| Beeswax | 50.00 mg |
| Ammonium Glycyrrhizinate | 10.00 mg |
| Vegetable oil | q.s. to 800.00 mg |

EXAMPLE VII

Soft-gelatin Capsules for the Treatment of Cervical Tumor

| | |
|---|---|
| Sanguinarine luteate | 10.00 mg |
| Soy lecithin | 50.00 mg |
| Beeswax | 50.00 mg |
| Sodium succinyl-glycyrrhetate | 10.00 mg |
| Vegetable oil | q.s. to 800.00 mg |

EXAMPLE VIII

Oil-in-water Emulsion of phosphatidic acid Sanguinarine Salt for the Topical Treatment of Melanoma

| | |
|---|---|
| Di-palmitoylphosphatidic acid sanguinarine salt | 0.40 g |
| Propylene glycol | 10.00 g |
| Isopropyl myristate | 5.00 g |
| Cetyl alcohol | 5.00 g |
| Polysorbate 80 | 3.00 g |
| Carbomer | 0.40 g |
| Methyl parahydroxy benzoate | 0.10 g |
| Propyl parahydroxy benzoate | 0.05 g |
| Purified water | q.s. to 100 g |

The invention claimed is:

1. A method for treating tumors comprising, administering a therapeutically effective amount of a salt of benzophenanthridine alkaloids to a patient in need thereof, wherein the benzophenanthridine alkaloids are selected from the group consisting of sanguinarine, chelerythrine, and chelidonine and the salt of benzophenanthridine alkaloids is selected from the group consisting of a salt with luteic acid, a salt with hyaluronic acid and a salt with a phosphatidic acid.

2. The method as claimed in claim 1, wherein the alkaloid is sanguinarine.

3. The method as claimed in claim 1, wherein the salt of benzophenanthridine alkaloids is a salt with luteic acid or a salt with a phosphatidic acid.

4. The method as claimed in claim 3, wherein the salt of benzophenanthridine alkaloid with luteic acid is sanguinarine luteate.

5. The method as claimed in claim 3, wherein the salt of benzophenanthridine alkaloids is a salt of sanguinarine with a phosphatidic acid.

6. The method as claimed in claim 1, wherein the benzophenanthridine alkaloids are administered in the form of nanoparticles consisting of complexes of said benzophenanthridine alkaloids with albumin.

7. The method as claimed in claim 1, wherein the tumors are originated from hyperproliferation of multiresistant tumor stem cells.

8. The method as claimed in claim 1, wherein the tumors are tumors of oropharynx, or tumors of head and neck, or cervical tumors, or melanoma.

* * * * *